US009655876B2

(12) United States Patent
Sonoke

(10) Patent No.: US 9,655,876 B2
(45) Date of Patent: May 23, 2017

(54) LIQUID COMPOSITION CONTAINING TAXANE-BASED ACTIVE INGREDIENT, PROCESS FOR PRODUCING SAME, AND LIQUID PREPARATION

(71) Applicant: FUJIFILM CORPORATION, Minato-ku, Tokyo (JP)

(72) Inventor: Shirou Sonoke, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 0 days.

(21) Appl. No.: 14/590,991

(22) Filed: Jan. 7, 2015

(65) Prior Publication Data

US 2015/0126594 A1 May 7, 2015

Related U.S. Application Data

(63) Continuation of application No. PCT/JP2013/068668, filed on Jul. 8, 2013.

(30) Foreign Application Priority Data

Jul. 19, 2012 (JP) ................ 2012-161001

(51) Int. Cl.
| | | |
|---|---|---|
| A61K 31/337 | (2006.01) | |
| A61K 9/00 | (2006.01) | |
| A61K 9/08 | (2006.01) | |
| A61K 47/10 | (2017.01) | |
| A61K 47/12 | (2006.01) | |
| A61K 47/14 | (2017.01) | |
| A61K 47/26 | (2006.01) | |
| A61K 47/44 | (2017.01) | |

(52) U.S. Cl.
CPC .......... *A61K 31/337* (2013.01); *A61K 9/0019* (2013.01); *A61K 9/08* (2013.01); *A61K 47/10* (2013.01); *A61K 47/12* (2013.01); *A61K 47/14* (2013.01); *A61K 47/26* (2013.01); *A61K 47/44* (2013.01)

(58) Field of Classification Search
CPC .................................... A61K 31/337
USPC ................ 514/449; 549/510, 511
See application file for complete search history.

(56) References Cited

U.S. PATENT DOCUMENTS

| 8,044,093 B2* | 10/2011 | Hao ............... 514/449 |
|---|---|---|
| 2009/0118354 A1 | 5/2009 | Liu et al. |
| 2010/0267818 A1 | 10/2010 | Yoo et al. |
| 2010/0297194 A1 | 11/2010 | Catron et al. |
| 2011/0269829 A1 | 11/2011 | Nabeta |
| 2012/0129922 A1 | 5/2012 | Palepu |
| 2013/0052241 A1 | 2/2013 | Nabeta |

FOREIGN PATENT DOCUMENTS

| JP | 2008-543789 A | 12/2008 |
|---|---|---|
| JP | 2011-513299 A | 4/2011 |
| WO | 2007/020085 A2 | 2/2007 |
| WO | 2009/047794 A2 | 4/2009 |
| WO | 2010/038776 A1 | 4/2010 |
| WO | 2011/079127 A1 | 6/2011 |
| WO | 2011/139899 A | 11/2011 |

OTHER PUBLICATIONS

International Search Report issued in International Application No. PCT/JP2013/068668 on Sep. 10, 2013.
Written Opinion of the ISA issued in International Application No. PCT/JP2013/068668 on Sep. 10, 2013.
Chinese Office Action dated Nov. 30, 2015 in corresponding Chinese Patent Application.
Japanese Office Action dated Jul. 21, 2015, issued in corresponding Japanese Patent Application.
Partial Supplementary European Search Report dated Feb. 19, 2016, issued in corresponding EP Patent Application.
Serva Electrophoresis Gmbh: "SPEZIFIKATION Polysorbat 80VG", Nov. 15, 2004 (Nov. 15, 2004), Retrieved from the Internet: URL:http://search.cosmobio.co.jp/cosmo_search_p/search_gate2/docs/SER_/33116.20050426.pdf.
Extended European Search Report dated Apr. 28, 2016 in corresponding European Patent Application.
Japanese Office Action dated Aug. 30, 2016 in corresponding Japanese Patent Application No. 2015-220996 and a Partial English Translation thereof.
Chinese Office Action dated Jun. 13, 2016 in corresponding Chinese Patent Application and Partial English Translation thereof.
Pharmaceutical Research, vol. 21, No. 2, Feb. 2004: 201-30 Abstract, p. 214, p. 221-222.
English language translation of the following: Office action dated Jan. 6, 2017 from the TIPO in a Taiwan patent application No. 102125332 related to the instant patent application.
Chinese Office Action dated Jan. 6, 2017 in corresponding Chinese Patent Application No. 201380037557.6 and a Partial English Translation thereof.
Japanese Office Action dated Feb. 28, 2017 in corresponding Japanese Patent Application No. 2015-220996 and a Partial English Translation thereof.

\* cited by examiner

*Primary Examiner* — Taofiq A Solola
(74) *Attorney, Agent, or Firm* — Solaris Intellectual Property Group, PLLC

(57) ABSTRACT

A liquid composition which includes a taxane-based active ingredient (a) selected from the group consisting of docetaxel and a derivative thereof; at least one glycol (b); and at least one surfactant component (c) selected from the group consisting of a polysorbate, a polyoxyethylene glycol ester, and a polyoxyethylene castor oil derivative, in which a volume ratio of the glycol (b) to the surfactant component (c) is in a range of form 45/55 to 55/45, and a total content of the glycol (b) and the surfactant component (c) with respect to a total volume of the liquid composition is 95% (v/v) or more.

6 Claims, No Drawings

LIQUID COMPOSITION CONTAINING TAXANE-BASED ACTIVE INGREDIENT, PROCESS FOR PRODUCING SAME, AND LIQUID PREPARATION

CROSS-REFERENCE TO RELATED APPLICATIONS

This application is a continuation application of International Application No. PCT/JP2013/068668, filed Jul. 8, 2013, the disclosure of which is incorporated herein by reference in its entirety. Further, this application claims priority from Japanese Patent Application No. 2012-161001, filed Jul. 19, 2012, the disclosure of which is incorporated herein by reference in its entirety.

TECHNICAL FIELD

The invention relates to a liquid composition containing a taxane-based active ingredient, a method of producing the liquid composition, and a liquid preparation.

BACKGROUND ART

Docetaxel, which is a taxane-based drug used as an anti-malignant tumor agent, is administered by intravenous drip infusion to patents.

Since taxane-based drugs are poor-solubility drugs, the taxane-based drugs are solubilized using a solubilizer such as a polysorbate or alcohol when administered by intravenous drip infusion. However, there are concerns regarding adverse effects such as hypersensitivity with respect to the use of such a solubilizer.

As an approach to such a problem, Korean Registered Patent Publication No. 136722 (Patent Document 1) discloses a method of producing a liquid composition that contains a taxane-based drug and that is substantially free of ethanol, by dissolving the taxane-based drug in the presence of ethanol and then distilling away the ethanol.

SUMMARY OF INVENTION

Technical Problem

It is difficult to rapidly mix an injection preparation containing a taxane-based drug prepared according to the method described in Patent Document 1 into an infusion liquid used for intravenous drip infusion. In addition, precipitation from the injection preparation containing a taxane-based drug prepared according to the method described in Patent Document 1 may occur during storage.

In such circumstances, the development of a liquid composition that includes a taxane-based drug and is substantially free of ethanol and that can be rapidly mixed into an infusion liquid has been greatly anticipated.

An object of the invention is to provide a liquid composition that includes a taxane-based active ingredient and is substantially free of ethanol and that can be rapidly mixed into an infusion liquid that is used for intravenous drip infusion, and to provide a method of producing the liquid composition. An object of another embodiment of the invention is to provide a liquid composition in which generation of degraded products is suppressed and storage stability can be maintained over a long period.

Solution to Problem

Specific means for solving the above problems are as follows.

<1> A liquid composition, including:
a taxane-based active ingredient (a) selected from the group consisting of docetaxel and a derivative thereof;
at least one glycol (b); and
at least one surfactant component (c) selected from the group consisting of a polysorbate, a polyoxyethylene glycol ester, and a polyoxyethylene castor oil derivative,
in which a volume ratio of the glycol (b) to the surfactant component (c) is in a range of from 45/55 to 55/45, and a total content of the glycol (b) and the surfactant component (c) with respect to a total volume of the liquid composition is 95% (v/v) or more.

<2> The liquid composition according to <1>, further including an organic acid (d).

<3> The liquid composition according to <1> or <2>, in which the taxane-based active ingredient is docetaxel.

<4> The liquid composition according to any one of <1> to <3>, in which a concentration of the taxane-based active ingredient is from 16 mg/mL to 24 mg/mL.

<5> The liquid composition according to any one of <1> to <4>, in which the glycol includes a glycol having a molecular weight of from 20 to 600.

<6> The liquid composition according to any one of <1> to <5>, in which the glycol includes a polyethylene glycol having a molecular weight of from 20 to 600.

<7> The liquid composition according to any one of <1> to <6>, in which the glycol includes polyethylene glycol 300.

<8> The liquid composition according to any one of <1> to <7>, in which the surfactant component includes polysorbate 80.

<9> The liquid composition according to any one of <1> to <8>, in which the surfactant component is a polysorbate having a peroxide value of 5 meq/kg or less.

<10> The liquid composition according to any one of <2> to <9>, in which the organic acid includes anhydrous citric acid.

<11> The liquid composition according to any one of <2> to <10>, in which a concentration of the organic acid is from 1.0 mg/mL to 4.0 mg/mL.

<12> The liquid composition according to any one of <1> to <11>, which has a pH of within a range of from 3.0 to 4.5 when diluted fivefold with distilled water.

<13> The liquid composition according to any one of <1> to <12>, in which a content of ethanol with respect to a total volume of the liquid composition is less than 1% (v/v).

<14> A liquid composition including:
at least one taxane-based active ingredient (a) selected from the group consisting of docetaxel and a derivative thereof;
at least one glycol (b); and
at least one surfactant component (c) selected from the group consisting of a polysorbate, a polyoxyethylene glycol ester, and a polyoxyethylene castor oil derivative,
in which the surfactant component has a peroxide value of 5 meq/kg or less.

<15> The liquid composition according to <14>, in which the taxane-based active ingredient is docetaxel.

<16> The liquid composition according to <14> or <15>, in which a volume ratio of the glycol to the surfactant component is in a range of from 45/55 to 55/45.

<17> The liquid composition according to any one of <14> to <16>, in which a total content of the glycol and the surfactant component with respect to a total volume of the liquid composition is 95% (v/v) or more.

<18> The liquid composition according to any one of <14> to <17>, in which the surfactant component is a polysorbate.

<19> The liquid composition according to any one of <14> to <18>, in which the surfactant component is polysorbate 80.

<20> The liquid composition according to any one of <14> to <19>, further including an organic acid (d).

<21> The liquid composition according to any one of <14> to <20>, in which a concentration of the taxane-based active ingredient is from 16 mg/mL to 24 mg/mL.

<22> The liquid composition according to any one of <14> to <21>, in which the glycol is a glycol having a molecular weight of from 20 to 600.

<23> The liquid composition according to any one of <14> to <22>, in which the glycol is a polyoxyethylene glycol having a molecular weight of from 20 to 600.

<24> The liquid composition according to any one of <14> to <23>, in which the glycol is polyethylene glycol 300.

<25> The liquid composition according to any one of <20> to <24>, in which the organic acid is citric acid.

<26> The liquid composition according to any one of <20> to <25>, in which a concentration of the organic acid is from 1.0 mg/mL to 4.0 mg/mL.

<27> The liquid composition according to any one of <14> to <26>, which has a pH of within a range of from 3.0 to 4.5 when diluted to fivefold with distilled water.

<28> The liquid composition according to any one of <14> to <27>, in which a content of ethanol with respect to a total volume of the liquid composition is less than 1% (v/v).

<29> A method of producing a liquid composition, the method including:
a heating and dissolving step of heating a mixed liquid including at least one taxane-based active ingredient (a) selected from the group consisting of docetaxel and a derivative thereof, at least one glycol (b), and at least one surfactant component (c) selected from the group consisting of a polysorbate, a polyoxyethylene glycol ester, and a polyoxyethylene castor oil derivative, without using a cosolvent, thereby dissolving the taxane-based active ingredient (a) in the mixed liquid.

<30> A method of producing a liquid composition, the method including:
a heating and dissolving step of heating a mixed liquid including at least one taxane-based active ingredient (a) selected from the group consisting of docetaxel and a derivative thereof, at least one glycol (b), and at least one surfactant component (c) selected from the group consisting of a polysorbate, a polyoxyethylene glycol ester, and a polyoxyethylene castor oil derivative, without using a cosolvent, thereby dissolving the taxane-based active ingredient (a) in the mixed liquid, wherein, in the mixed liquid, a volume ratio of the glycol (b) to the surfactant component (c) is in a range of from 45/55 to 55/45, and a total content of the glycol (b) and the surfactant component (c) with respect to a total volume of the mixed liquid is 95% (v/v) or more.

<31> The method according to <29> or <30>, further including a step of filter sterilizing a dissolved liquid obtained by the heating and dissolving step.

<32> The method according to any one of <29> to <31>, in which the mixed liquid further includes an organic acid (d).

<33> A liquid preparation including the liquid composition according to any one of <1> to <28> contained in a vial container, an amount of sodium that leaches from the vial container into water being 1 ppm or less when the vial container has been charged with water and heated at 121° C. for 60 minutes.

Advantageous Effects of Invention

According to the invention, a liquid composition that includes a taxane-based active ingredient and is substantially free of ethanol, and a method of producing the liquid composition are provided. The invention further provides a liquid composition that includes a taxane-based active ingredient and that can be rapidly mixed into an infusion liquid used for intravenous drip infusion, and a method of producing the liquid composition. According to the invention, a liquid composition in which generation of degraded products is suppressed and storage stability can be maintained over a long period and a method of producing the liquid composition can be provided.

DESCRIPTION OF EMBODIMENTS

The first embodiment of the liquid composition according to the invention is a liquid composition (hereinafter, sometimes referred to as "liquid composition I") including:
a taxane-based active ingredient (a) selected from the group consisting of docetaxel and a derivative thereof;
at least one glycol (b); and
at least one surfactant component (c) selected from the group consisting of a polysorbate, a polyoxyethylene glycol ester, and a polyoxyethylene castor oil derivative,
in which a volume ratio of the glycol (b) to the surfactant component (c) is in a range of form 45/55 to 55/45, and a total content of the glycol (b) and the surfactant component (c) with respect to a total volume of the liquid composition is 95% (v/v) or more.

The liquid composition I according to the invention includes a taxane-based active ingredient selected from the group consisting of docetaxel and a derivative thereof, together with a specific amount of glycol and a specific amount of surfactant component. Therefore, mixability of the liquid composition with respect to an infusion liquid used for intravenous drip infusion can be improved even when the liquid composition is substantially free of ethanol.

The second embodiment of the liquid composition according to the invention is a liquid composition (hereinafter, sometimes referred to as "liquid composition II") including:
at least one taxane-based active ingredient (a) selected from the group consisting of docetaxel and a derivative thereof;
at least one glycol (b); and
at least one surfactant component (c) selected from the group consisting of a polysorbate, a polyoxyethylene glycol ester, and a polyoxyethylene castor oil derivative,
in which the surfactant component has a peroxide value of 5 meq/kg or less.

The liquid composition II according to the invention includes a surfactant component having a peroxide value of 5 meq/kg or less. Therefore, the generation of degraded products can be suppressed and storage stability can be maintained over a long period.

The term "step" as used herein indicates not only a separate step but also a step that is not clearly distinguished from other step as long as the desired effect of the step is obtained therefrom.

In this specification, each numerical range specified using "(from) A to B" represents a range including the numerical values noted before and after "to" as the minimum value and the maximum value, respectively.

In this specification, in the reference to the amount of each ingredient in the composition, when the composition includes plural substances corresponding to an ingredient, the amount of the ingredient means the total amount of the plural substances unless otherwise specified.

The term "infusion liquid" used herein encompasses not only general infusion liquids used for intravenous drip infusion commonly used in clinical practice but also physiological saline. The physiological saline means saline that contains 0.9% (w/v) of sodium chloride.

In the invention, "% (v/v)" used regarding, for example, the mixing amount (concentration) of each component contained in the liquid composition according to the invention means a percentage of the volume (mL) of each component with respect to a 100 mL volume of the liquid composition (the following Equation 1a). Similarly, in a case in which the volume of each component is described with respect to the total volume of a liquid composition, "% (v/v)" means the volume (mL) of each component with respect to a 100 mL volume of the liquid composition unless otherwise specified. For example, the mixing amount of a component that is to be mixed at a volume of 1.0 mL into 100 mL of a liquid composition is describes as "1.0% (v/v)".

[volume of each component (mL)/100 mL volume of the whole composition]×100(%)   Equation 1a:

Hereinbelow, the invention is explained in details.

Liquid Composition

The liquid composition I according to the invention includes a taxane-based active ingredient (a) selected from the group consisting of docetaxel and a derivative thereof; at least one glycol (b); and at least one surfactant component (c) selected from the group consisting of a polysorbate, a polyoxyethylene glycol ester, and a polyoxyethylene castor oil derivative, in which a volume ratio of the glycol (b) to the surfactant component (c) is in a range of form 45/55 to 55/45, and a total content of the glycol (b) and the surfactant component (c) with respect to a total volume of the liquid composition is 95% (v/v) or more.

The liquid composition II includes at least one taxane-based active ingredient (a) selected from the group consisting of docetaxel and a derivative thereof; at least one glycol (b); and at least one surfactant component (c) selected from the group consisting of a polysorbate, a polyoxyethylene glycol ester, and a polyoxyethylene castor oil derivative, in which the surfactant component has a peroxide value of 5 meq/kg or less.

Hereinbelow, respective components contained in the liquid composition are explained. Here, the description regarding each of the components is common to the liquid composition I and the liquid composition II unless otherwise specified.

Taxane-Based Active Ingredient

The liquid composition according to the invention includes a taxane-based active ingredient selected from the group consisting of docetaxel and a derivative thereof.

The taxane-based active ingredient in the invention is at least one selected from the group consisting of docetaxel and a derivative thereof.

Docetaxel is a poor-solubility drug known as a taxane-based anti-tumor agent.

Examples of the derivative of docetaxel include those described in Japanese Patent No. 3950993, and also can be obtained in accordance with or according to the method described in International Publication No. WO 92/09589 or WO 93/06093, or EP 534708 A1, EP 558959 A1, or FR 2697019 A1.

The scope of the docetaxel and the derivative thereof encompasses pharmaceutically acceptable salts and hydrates thereof. Examples thereof include docetaxel trihydrate.

The taxane-based active ingredient is generally used singly, but may be used in mixture of two or more kinds thereof.

The taxane-based active ingredient is preferably docetaxel or docetaxel trihydrate. From the viewpoint of solubility in the production of the liquid composition according to the invention, the taxane-based active ingredient is more preferably docetaxel trihydrate.

From the viewpoint of the mixability with respect to the infusion liquid, the concentration of the taxane-based active ingredient in the liquid composition is preferably from 16 mg/mL to 24 mg/mL, more preferably from 18 mg/mL to 23 mg/mL, and still more preferably from 19 mg/mL to 22 mg/mL.

Glycol

The liquid composition according to the invention includes at least one glycol.

From the viewpoint of safety for the human body and from the viewpoint of handling, the glycol is preferably one having a molecular weight of from 20 to 600, more preferably one having a molecular weight of from 50 to 400, and still more preferably one having a molecular weight of from 270 to 330.

Examples of the glycol include ethylene glycol, triethylene glycol, propylene glycol, a tetraglycol, butylene glycol, and a polyethylene glycol. From the viewpoint of safety for the human body, propylene glycol, butylene glycol, and a polyethylene glycol are preferable. In particular, from the viewpoint of safety for the human body in parenteral administration, propylene glycol and a polyethylene glycol are preferable.

Specific examples of the polyethylene glycol include polyethylene glycol 200, polyethylene glycol 300, polyethylene glycol 400, and polyethylene glycol 600.

Here, polyethylene glycol 200 is a mixture of polyethylene glycols having a molecular weight of from 180 to 220; polyethylene glycol 300 is a mixture of polyethylene glycols having a molecular weight of from 270 to 330; polyethylene glycol 400 is a mixture of polyethylene glycols having a molecular weight of from 360 to 440; and polyethylene glycol 600 is a mixture of polyethylene glycols having a molecular weight of from 640 to 660.

From the viewpoint of use results in parenteral administration, polyethylene glycol 400 and polyethylene glycol 300 are preferable. From the viewpoint of mixability in the production of the composition and mixability of the composition with an infusion liquid, polyethylene glycol 300 is more preferable.

In particular, polyethylene glycol 300 having an average molecular weight of from 280 to 320 is preferable; and polyethylene glycol 300 having an average molecular weight of from 285 to 315 is more preferable.

The average molecular weight of the polyethylene glycol can be measured in accordance with the method described in the Japanese Pharmacopoeia, sixteenth edition.

A commercially available glycol may be used as the glycol.

Examples of commercially available polyethylene glycol 400 include MACROGOL 400 (trade name, manufactured by Maruishi Pharmaceutical), SR PEG400 NF (trade name, manufactured by CRODA), and SUNBRIGHT DKH-04HB (trade name, manufactured by NOF Corporation).

Examples of commercially available polyethylene glycol 300 include SUNBRIGHT DKH-03HB (trade name, manufactured by NOF Corporation), SR PEG300 NF (trade name, manufactured by CRODA), and PEG 300 (trade name, manufactured by MERCK).

In the liquid composition, any kind of glycol may be used singly, or two or more kinds thereof may be used in combination. Here, the content of polyethylene glycol 300 with respect to the total glycol(s) is preferably 70% (v/v) or more, more preferably 80% (v/v) or more, and still more preferably 90% (v/v) or more.

The content of the glycol with respect to the total volume of the liquid composition is preferably from 45% (v/v) to 55% (v/v). In a case in which the content of the glycol with respect to the total volume of the liquid composition is 45% (v/v) or more, mixability of the liquid composition with the infusion liquid can be maintained. In a case in which the content of the glycol with respect to the total volume of the liquid composition is 55% (v/v) or less, decrease in affinity for the surfactant component can be suppressed. As a result, the liquid composition can be used for drug production.

The content of the glycol with respect to the total volume of the liquid composition is more preferably from 47.5% (v/v) to 52.5% (v/v).

Surfactant Component

The liquid composition according to the invention includes the surfactant component selected from the group consisting of a polysorbate, a polyoxyethylene glycol ester, and a polyoxyethylene castor oil derivative.

The surfactant component selected from the group consisting of a polysorbate, a polyoxyethylene glycol ester, and a polyoxyethylene castor oil derivative can be preferably used since safety thereof for various races in the case of being used in parenteral administration is confirmed on a worldwide scale.

Specific examples of the polysorbate include polysorbate 20 and polysorbate 80.

Any commercially available polysorbate may be used as the polysorbate. Examples of commercially available polysorbate 80 include Tween 80 HP (trade name, manufactured by CRODA), NIKKOL TO-10MV (trade name, manufactured by Nikko Chemicals Co., Ltd.), MONTANOX 80 PPI (trade name, manufactured by SEPPIC), MONTANOX 80 API (trade name, manufactured by SEPPIC), POLYSORBATE 80GS (trade name, manufactured by NOF Corporation), and POLYSORBATE 80HX2 (trade name, manufactured by NOF Corporation).

From the viewpoint of use results in parenteral administration, the polyoxyethylene glycol ester is preferably one having an average addition mole number of ethylene oxide of from 3 to 60, and more preferably one having an average addition mole number of ethylene oxide of from 30 to 40.

Any commercially available polyoxyethylene glycol ester may be used as the polyoxyethylene glycol ester, and examples thereof include CREMOPHOR EL-P (trade name, manufactured by BASF), CREMOPHOR EL (trade name, manufactured by BASF), and NIKKOL CO-10 (trade name, manufactured by Nikko Chemicals Co., Ltd.).

The polyoxyethylene castor oil derivative is a non-ionic surfactant that can be obtained by the addition polymerization of a hydrogenated castor oil, in which a hydrogen atom is added to a double bond of a castor oil, with ethylene oxide. Specific examples thereof include polyoxyethylene hydrogenated castor oil 50 and polyoxyethylene hydrogenated castor oil 60.

The commercially available polyoxyethylene castor oil derivative may be used as the polyoxyethylene castor oil derivative, and examples thereof include NIKKOL HCO-50 (trade name, manufactured by Nikko Chemicals Co., Ltd.) and NIKKOL HCO-60 (trade name, manufactured by Nikko Chemicals Co., Ltd.).

The surfactant component is preferably CREMOPHOR EL, HCO-60, or polysorbate 80, more preferably CREMOPHOR EL or polysorbate 80, and still more preferably polysorbate 80, since the safety when used in parenteral formulation is confirmed.

In the liquid composition, the surfactant component may be used singly, or two or more kinds thereof may be used in combination. The content of polysorbate 80 with respect to the total volume of the surfactant component is preferably 70% (v/v) or more, more preferably 80% (v/v) or more, and still more preferably 90% (v/v) or more.

In the liquid composition I, the surfactant component is preferably one having a peroxide value of 5 meq/kg or less. In a case in which the surfactant component having a peroxide value of 5 meq/kg or less is contained, the generation of degraded products can be suppressed.

The surfactant component is more preferably one having a peroxide value of 3 meq/kg or less.

In the specification, the peroxide value of the surfactant component is measured in accordance with the potentiometric titration method described in European Pharmacopoeia, edition 7.0.

From the viewpoint of suppressing the generation of degraded products efficiently, the surfactant component is preferably a polysorbate having a peroxide value of 5 meq/kg or less, and more preferably polysorbate 80 having a peroxide value of 5 meq/kg or less.

In the liquid composition II, the surfactant component has a peroxide value of 5 meq/kg or less. In a case in which the surfactant component has a peroxide value of more than 5 meq/kg, the generation of degraded products cannot be suppressed.

The surfactant component is preferably one having a peroxide value of 3 meq/kg or less.

In the specification, the peroxide value of the surfactant component is measured in accordance with the potentiometric titration method described in European Pharmacopoeia, edition 7.0.

From the viewpoint of suppressing the generation of degraded products effectively, the surfactant component is preferably a polysorbate having a peroxide value of 5 meq/kg or less, and more preferably polysorbate 80 having a peroxide value of 5 meq/kg or less.

The content of the surfactant component with respect to the total volume of the liquid composition is preferably from 45% (v/v) to 55% (v/v). In a case in which the content of the surfactant component with respect to the total volume of the liquid composition is 45% (v/v) or more, the affinity of the surfactant component for the glycol can be maintained and the liquid composition can be used for drug production. In a case in which the content of the surfactant component with respect to the total volume of the liquid composition is 55% (v/v) or less, miscibility with the infusion liquid can be maintained.

The content of the surfactant component with respect to the total volume of the liquid composition is more preferably from 47.5% (v/v) to 52.5% (v/v).

In the liquid composition I according to the invention, the volume ratio of the glycol to the surfactant component is in a range of form 45/55 to 55/45. In a case in which the volume ratio of the glycol to the surfactant component is less than 45/55, miscibility of the liquid composition I with the infusion liquid is decreased. In a case in which the volume ratio of the glycol to the surfactant component is more than 55/45, affinity of the surfactant for the glycol is decreased and the liquid composition I cannot be used for drug production.

The volume ratio of the glycol to the surfactant component is preferably in a range of form 47.5/52.5 to 52.5/47.5.

In the liquid composition II according to the invention, the volume ratio of the glycol to the surfactant component is preferably in a range of form 45/55 to 55/45. In a case in which the volume ratio of the glycol to the surfactant component is 45/55 or more, the decrease in mixability of the liquid composition with the infusion liquid can be suppressed. In a case in which the volume ratio of the glycol to the surfactant component is 55/45 or less, the decrease in affinity of the surfactant for the glycol can be suppressed and the liquid composition II can be used for drug production.

The volume ratio of the glycol to the surfactant component is more preferably in a range of form 47.5/52.5 to 52.5/47.5.

In the liquid composition I according to the invention, the total content of the glycol and the surfactant component with respect to the total volume of the liquid composition I is 95% (v/v) or more. In a case in which the total content of the glycol and the surfactant component is less than 95% (v/v), the stability of docetaxel is deteriorated.

From the viewpoint of the stability of the dissolved docetaxel, the total content of the glycol and the surfactant component with respect to the total volume of the liquid composition I is preferably 99% (v/v) or more.

In the liquid composition II according to the invention, the total content of the glycol and the surfactant component with respect to the total volume of the liquid composition I is preferably 95% (v/v) or more. In a case in which the total content of the glycol and the surfactant component is 95% (v/v) or more, the stability of docetaxel can be maintained.

From the viewpoint of the stability of the dissolved docetaxel, the total content of the glycol and the surfactant component with respect to the total volume of the liquid composition II is more preferably 99% (v/v) or more.

Organic Acid

It is preferable that the liquid composition according to the invention include an organic acid.

The inclusion of the organic acid enables stabilization of the taxane-based active ingredient.

The organic acid is not particularly limited as long as it is a pharmaceutically acceptable organic acid, and examples thereof include formic acid, acetic acid, trifluoroacetic acid, fumaric acid, oxalic acid, tartaric acid, maleic acid, critic acid, succinic acid, malic acid, methanesulfonic acid, benzenesulfonic acid, p-toluenesulfonic acid, aspartic acid, glutamic acid, and ascorbic acid. In particular, the organic acid is preferably tartaric acid, critic acid, or ascorbic acid. From the viewpoint of the effect of stabilizing the taxane-based active ingredient, critic acid is more preferable. It is preferable to add anhydrous citric acid as critic acid, since it is possible to obtain a more potent effect of stabilizing the taxane-based active ingredient.

A commercially available organic acid may be used as the organic acid, and examples thereof include ANHYDROUS CITRIC ACID (trade name, manufactured by MERCK), CITRIC ACID MONOHYDRATE (trade name, manufactured by Wako Pure Chemical Industries), and ASCORBIC ACID (trade name, manufactured by Wako Pure Chemical Industries).

In the liquid composition, the organic acid may be used singly, or two or more kinds thereof may be used in combination. The content of the critic acid in the total volume of the organic acid is preferably 70% (w/w) or more, more preferably 80% (w/w) or more, and still more preferably 90% (w/w) or more.

From the viewpoint of stabilizing the taxane-based active ingredient, the concentration of the organic acid in the liquid composition is preferably from 1.0 mg/mL to 4.0 mg/mL, more preferably from 1.5 mg/mL to 3.0 mg/mL, and still more preferably from 1.75 mg/mL to 2.5 mg/mL.

Other Components

The liquid composition may include other pharmaceutically acceptable components in addition to the taxane-based active ingredient, the specific amount of glycol, and the specific amount of surfactant component.

Examples of the other components include, but not limited to, a pH adjusting agent and a stabilizing agent (such as sodium pyrosulphite).

Liquid Composition

The liquid composition according to the invention is substantially free of ethanol, and therefore can be safely administered to a patient having a tolerance for alcohol as well as a patient having hypersensitivity to alcohol.

The liquid composition preferably has a pH of within a range of from 3.0 to 4.5 when diluted to fivefold based on mass with distilled water. It is preferable for the liquid composition to have a pH of within the above range when diluted, since the degradation of the taxane-based active ingredient is suppressed and favorable stability is obtained. Furthermore, it is preferable for the liquid composition to have a pH of within the above range when diluted, since favorable mixability of the composition with the infusion liquid used for intravenous drip infusion is obtained and vascular pain or the like is less likely to be induced when the liquid composition is mixed into the infusion liquid and administered by intravenous drip infusion to patents. The pH of the liquid composition when diluted is more preferably within a range of from 3.0 to 4.0

In the invention, the distilled water used for measuring the pH means water distilled with a distiller.

A commercially available distilled water may be used as the distilled water, and examples thereof include OTSUKA DISTILLED WATER FOR INJECTION (trade name, manufactured by Otsuka Pharmaceutical Co., Ltd.) and DISTILLED WATER (trade name, manufactured by Wako Pure Chemical Industries).

In the liquid composition, the content of ethanol with respect to the total volume of the liquid composition is preferably less than 1% (v/v). In a case in which the content of ethanol is less than 1% (v/v), the liquid composition can be safely administered even to a patient having hypersensitivity to alcohol. The content of ethanol with respect to the total volume of the liquid composition is more preferably less than 0.5% (v/v), and still more preferably less than 0.1% (v/v).

The content of ethanol can be confirmed by a conventional method. More specifically, it can be confirmed by a gas-chromatographic method.

The liquid composition can be prepared by adding the taxane-based active ingredient to the specific amounts of glycol and surfactant component, and then stirring and dissolving the mixed liquid while heating until the mixed liquid turns into a homogenous and transparent liquid.

The liquid composition can be used as a drug for treating cancers. Examples of the kind of the cancer to which the drug is administered include breast cancer, non-small cell lung cancer, gastric cancer, head and neck cancer, ovarian cancer, esophageal cancer, endometrial cancer, and prostate cancer.

Method of Producing Liquid Composition

The production method according to the invention include a heating and dissolving step of heating a mixed liquid including a taxane-based active ingredient (a) selected from the group consisting of docetaxel and a derivative thereof, at least one glycol (b), and at least one surfactant component (c) selected from the group consisting of a polysorbate, a polyoxyethylene glycol ester, and a polyoxyethylene castor oil derivative, without using a cosolvent to dissolve the taxane-based active ingredient (a) in the mixed liquid (hereinafter, sometimes referred to as "production method I").

Since the production method I of the liquid composition according to the invention include dissolving the glycol and the surfactant component by heating, the liquid composition can be produced without using a cosolvent even when the poor-solubility taxane-based active ingredient is included. Furthermore, since no cosolvent is used in this production method, the step of removing the solvent is not required.

In the production method I of the liquid composition, the volume ratio of the glycol (b) to the surfactant component (c) is preferably from 4/6 to 7/3.

In another embodiment, the production method according to the invention include a heating and dissolving step of heating a mixed liquid including a taxane-based active ingredient (a) selected from the group consisting of docetaxel and a derivative thereof, at least one glycol (b), and at least one surfactant component (c) selected from the group consisting of a polysorbate, a polyoxyethylene glycol ester, and a polyoxyethylene castor oil derivative, in which the volume ratio of the glycol (b) to the surfactant component (c) is in a range of form 45/55 to 55/45, and the total content of the glycol (b) and the surfactant component (c) with respect to the total volume of the mixed liquid is 95% (v/v) or more, without using a cosolvent to dissolve the taxane-based active ingredient (a) in the mixed liquid (hereinafter, sometimes referred to as "production method II"). Since no cosolvent is used in this production method, the step of removing the solvent is not required.

Since the production method II of the liquid composition according to the invention include dissolving the specific amounts of glycol and surfactant component by heating, the liquid composition can be produced without using a cosolvent even when the poor-solubility taxane-based active ingredient is included.

Hereinbelow, each of the steps in the production method of the liquid composition is described. Here, the description regarding each of the steps is common to the production method I and the production method II unless otherwise specified.

The cosolvent means an organic solvent having a boiling point of 120° C. or lower. Examples thereof include ethanol, acetone, methanol, and acetonitrile.

Heating and Dissolving Step

In the heating and dissolving step, a mixed liquid including the taxane-based active ingredient, the glycol, and the surfactant component is used to dissolve the taxane-based active ingredient in the mixed liquid while heating until the mixed liquid turns into a homogenous and transparent liquid.

From the viewpoint of stabilizing the taxane-based active ingredient and adjusting the pH, the mixed liquid may include the organic acid (d).

In the heating and dissolving step, the dissolving is preferably conducted under a heating condition of from 30° C. to 70° C., and more preferably conducted under a heating condition of from 35° C. to 50° C.

The heating and dissolving may be conducted while stirring.

A conventional method may be used as the stirring method. Examples thereof include stirring by a stirrer bar using a magnetic stirrer, and a stirring by a motor-driven stirring blade using a THREE-ONE MOTOR (manufactured by HEIDON).

The duration of the dissolving is not particularly limited as long as the homogenous and transparent solution can be obtained. For example, the duration is preferably from 1 hour to 6 hours, and more preferably from 2 hours to 3 hours.

With respect to the taxane-based active ingredient (a), the glycol (b), the surfactant component (c), and the organic acid (d), the descriptions in the above for these are directly applied respectively.

Filter Sterilizing Step

In the filter sterilizing step, the dissolved liquid obtained by the heating and dissolving step is filter sterilized.

The filter sterilization can be conducted by a method generally used for preparing a drug for intravenous drip infusion. Examples of the method that can be used include a method using a 0.22 μm membrane filter, and a method using a pressure filtration apparatus.

Other Steps

The method of producing the liquid composition according to the invention may further include a step other than the heating and dissolving step and the filter sterilizing step if necessary.

In the method of producing the liquid composition, it is preferable that the liquid composition after the filter sterilizing step is injected into an airtight container and the container is sealed. For this reason, the method of producing the liquid composition may further include a step of injecting the liquid composition into an airtight container and sealing the container (hereinafter, sometimes simply referred to as "productizing step").

Examples of the airtight container include a vial container, an ampule, and a syringe. In particular, from the viewpoint of handling in clinical practice, the vial container is preferable. Preferable examples of the vial container include low alkaline leaching ones. The vial container is more preferably one having an amount of sodium that leaches from the vial container into water of 1 ppm or less when the vial container has been charged with water and heated at 121° C. for 60 minutes.

A series of steps, namely the heating and dissolving step, the filter sterilizing step, and the productizing step, may be conducted in the presence of nitrogen gas with an oxygen concentration of 1.0% (v/v) or less. This is preferable since the stability of the liquid composition can be maintained for a prolong period.

It is preferable to conduct a series of steps in the presence of nitrogen gas with an oxygen concentration of 0.5% (v/v) or less, and more preferable to conduct a series of steps in the presence of nitrogen gas with an oxygen concentration of 0.1% (v/v) or less.

In another embodiment of the production method according to invention, the production method may include a heating and dissolving step of heating a mixed liquid including the at least one taxane-based active ingredient (a) selected from the group consisting of docetaxel and a derivative thereof, the at least one glycol (b), and the at least one surfactant component (c) selected from the group consisting of a polysorbate, a polyoxyethylene glycol ester, and a polyoxyethylene castor oil derivative, in which the surfactant component has a peroxide value of 5 meq/kg or less, to dissolve the taxane-based active ingredient (a) in the mixed liquid.

As a result, the generation of degraded products can be suppressed and the liquid composition in which storage stability can be maintained over long periods can be obtained.

Liquid Preparation

The liquid preparation according to the invention is a liquid preparation including the above-described liquid composition I or II contained in a vial container, an amount of sodium that leaches from the vial container into water being 1 ppm or less when the vial container has been charged with water and heated at 121° C. for 60 minutes.

In a case in which such a vial container is used, the generation of degraded products is suppressed and the storage stability of the liquid composition is maintained over a long period.

The amount of sodium leaching out can be measured by a conventional method. Examples thereof include a method using an atomic absorption spectrometer.

A commercially available vial container may be used as the vial container having an amount of sodium that leaches from the vial container into water is 1 ppm or less when the vial container has been charged with water and heated at 121° C. for 60 minutes. Examples thereof that can be used include a vial container which has been treated at a temperature lower than the usual glass forming temperature such as a low-temperature treated vial container (manufactured by Nichiden-Rika Glass Co., Ltd., Fuji Glass Co., Ltd, or Daiwa Special Glass Co., Ltd.), a vial container in which the alkaline component is removed from the glass surface with an organic acid such as a VIST treated vial container (manufactured by Daiwa Special Glass Co., Ltd.), and a vial container in which the glass surface is coated with an $SiO_2$ film such as a solicoat treated vial container manufactured by Fuji Glass Co., Ltd)

From the viewpoint of handling in clinical practice, the viscosity of the liquid preparation at 25° C. is preferably 300 mPa·s or less. The liquid preparation having a viscosity of within the above range is preferable, since the pressure at which the liquid preparation is drawn with a syringe or the like can be reduced.

The viscosity of the liquid preparation can be confirmed by a conventional method. Specific examples thereof include a method using a rotatory viscometer as described in the Japanese Pharmacopoeia, sixteenth edition.

EXAMPLES

Hereinafter, the invention is described more specifically with reference to the examples. However, the invention is not limited to these examples.

Example 1

Preparation of Liquid Preparation 42.7 mg of docetaxel trihydrate and 3.75 mg of an organic acid (anhydrous citric acid, manufactured by MERCK) were weighed into a clean vial container. To the vial container, 1.0 mL of glycol (polyethylene glycol 300:PEG 300, average molecular weight of from 285 to 315; manufactured by MERCK) and 1.0 mL of a surfactant (polysorbate 80, manufactured by SEPPIC) were added (total volume: 2.0 mL). Subsequently, the mixture was stirred to dissolve in the presence of nitrogen gas (oxygen concentration: 0.0% (v/v)) under a heating condition of 35° C. until the mixture turned into a homogenous and transparent solution.

In a nitrogen atmosphere, the obtained liquid composition was enclosed in the vial container, and the vial container was capped and stored until being subjected to filter sterilization.

The liquid composition enclosed and stored in the vial container was filter sterilized using a hydrophobized PVDF filter with a 0.2 μm pore size (trade name: DURAPORE, manufactured by Merck Millipore). Subsequently, the liquid composition obtained by the filter sterilization was charged into a low temperature treated vial container (manufactured by Nichiden-Rika Glass Co., Ltd.) in the presence of nitrogen gas (oxygen concentration: 0.0% (v/v)) and capped with a TEFLON (registered trade name) coated chlorobutyl rubber stopper, thereby obtaining a liquid preparation. The viscosity of the liquid preparation at 25° C. was 200 mPa·s.

0.1 g of the liquid composition prepared by heating and stirring the taxane-based active ingredient and the organic acid, and the specific amounts of glycol and surfactant component was diluted fivefold based on mass with 0.4 mL of distilled water (manufactured by Wako Pure Chemical Industries), and the pH value of the diluted composition was measured. The measured value is shown in Table 1.

Evaluation (1) Manufacturing Suitability

Time Required for Dissolving With regard to a mixed solution including the taxane-based active ingredient and the organic acid, and the specific amounts of glycol and surfactant component, the time required for turning the mixed solution into a homogenous and clear solution during heating and stirring was determined. The evaluation result is shown in Table 3 ("H" in the table indicates hour).

Here, whether the mixed solution turned into a homogenous and clear solution was visually determined. More specifically, the appearance of the mixed solution was visually observed and the time at which an insoluble residue was disappeared was determined as the completion of the dissolution.

Appearance Observation

The taxane-based active ingredient and the organic acid, and the specific amounts of glycol and surfactant component were heated and stirred, and the appearance of the obtained liquid composition after 12 hours was observed.

The case in which the homogenous solution was obtained was evaluated as "A", and the case in which the solution was separated was evaluated as "B". The evaluation result is shown in Table 4.

(2) Mixability with Infusion Liquid

The obtained liquid preparation was added to a physiological saline such that the docetaxel concentration is about 0.77 mg/mL, and the resultant was then stirred with a ROTATOR RT-50 manufactured by TAITEC. The mixability of the liquid preparation with the infusion liquid used for intravenous drip infusion after 1 minute of the stirring was evaluated.

By the visual observation, the case in which a large amount of gel materials were remained in the infusion liquid after 1 minute of the stirring was evaluated as "C", the case in which a small amount of gel materials were remained in the infusion liquid after 1 minute of the stirring was evaluated as "B", and the case in which the liquid preparation was mixed with the infusion liquid after 1 minute of the stirring was evaluated as "A". The evaluation result is shown in Table 5.

Examples 2 and 3, and Reference Examples 1 to 7

Each of liquid preparations of Examples 2 and 3 and Reference Examples 1 to 7 was obtained in a manner similar to Example 1, except that the amounts of respective components were changed to the amounts shown in Tables 1 and 2. The measured pH values of the liquid compositions are shown in Tables 1 and 2.

Examples 2 and 3 and Reference Examples 1 to 7 were used in the evaluation similarly to Example 1. The evaluation results are shown in Tables 3 to 5.

Here, Reference Example 1 is TAXOTERE (registered trade name), which is commercially available and which is an injectable docetaxel hydrate.

TABLE 1

|  | Example 1 | Example 2 | Example 3 |
|---|---|---|---|
| Polysorbate 80 (PS 80) [mL] | 1.0 | 1.1 | 0.9 |
| PEG 300 [mL] | 1.0 | 0.9 | 1.1 |
| Anhydrous citric acid [mg] | 3.75 | 3.75 | 3.75 |
| Docetaxel trihydrate [mg] | 42.7 | 42.7 | 42.7 |
| PS 800/PEG 300 [vol/vol] | 50/50 | 55/45 | 45/55 |
| pH value | 3.5 | 3.6 | 3.6 |

TABLE 2

|  | Reference Example 1 | Reference Example 2 | Reference Example 3 | Reference Example 4 | Reference Example 5 | Reference Example 6 | Reference Example 7 |
|---|---|---|---|---|---|---|---|
| Polysorbate 80 (PS 80) [mL] | 0.5 | 1.8 | 1.4 | 1.2 | 1.15 | 0.8 | 0.6 |
| PEG 300 [mL] | 0 | 0.2 | 0.6 | 0.8 | 0.85 | 1.2 | 1.4 |
| Anhydrous citric acid [mg] | 0 | 3.75 | 3.75 | 3.75 | 3.78 | 3.75 | 3.75 |
| Docetaxel trihydrate [mg] | 21.4 | 42.7 | 42.7 | 42.7 | 42.7 | 42.7 | 42.7 |
| PS 800/PEG 300 [vol/vol] | 100/0 | 90/10 | 70/30 | 60/40 | 57.5/42.5 | 40/60 | 30/70 |
| pH value | 3.7 | 3.5 | 3.6 | 3.5 | 3.6 | n.t. | n.t. |

TABLE 3

|  | Example 1 | Example 2 | Example 3 | Reference Example 1 | Reference Example 2 | Reference Example 3 | Reference Example 4 | Reference Example 5 | Reference Example 6 | Reference Example 7 |
|---|---|---|---|---|---|---|---|---|---|---|
| PS 800/PEG 300 [vol/vol] | 50/50 | 55/45 | 45/55 | 100/0 | 90/10 | 70/30 | 60/40 | 57.5/42.5 | 40/60 | 30/70 |
| Time required for dissolving | 2 H | 2 H | 2 H | n.t. | 5 H | 3 H | 2 H | 2 H | 2 H | 2 H |
| Evaluation | A | A | A | n.t. | C | B | A | A | A | A |

* n.t.: not tested

From the result shown in Table 3, it was found that a liquid composition that includes docetaxel and is free of ethanol can be prepared by heating the mixture in which polyethylene glycol 300 is added such that the composition ratio (% (v/v)) of Polysorbate 80 to polyethylene glycol 300 is from 6/4 to 3/7.

TABLE 4

|  | Example 1 | Example 2 | Example 3 | Reference Example 1 | Reference Example 2 | Reference Example 3 | Reference Example 4 | Reference Example 5 | Reference Example 6 | Reference Example 7 |
|---|---|---|---|---|---|---|---|---|---|---|
| PS 800/PEG 300 [vol/vol] | 50/50 | 55/45 | 45/55 | 100/0 | 90/10 | 70/30 | 60/40 | 57.5/42.5 | 40/60 | 30/70 |
| Appearance | Homogenous solution | Homogenous solution | Homogenous solution | Homogenous solution | Homogenous solution | Homogenous solution | Homogenous solution | Homogenous solution | Separated into two phases | Separated into two phases |
| Judgement | A | A | A | A | A | A | A | A | B | B |

TABLE 5

|  | Example 1 | Example 2 | Example 3 | Reference Example 1 | Reference Example 2 | Reference Example 3 | Reference Example 4 | Reference Example 5 | Reference Example 6 | Reference Example 7 |
|---|---|---|---|---|---|---|---|---|---|---|
| PS 800/PEG 300 [vol/vol] | 50/50 | 55/45 | 45/55 | 100/0 | 90/10 | 70/30 | 60/40 | 57.5/42.5 | 40/60 | 30/70 |
| 1 minute after | A | A | A | C | C | C | B | B | n.t. | n.t. |

* n.t.: not tested

From the result shown in Table 4, it was found that, in a case in which the composition ratio (% (v/v)) of polysorbate 80 to polyethylene glycol 300 is increased such that the addition amount of the polyethylene glycol 300 is 60% (v/v) or more, the obtained liquid composition is separated into two phases with time.

From the result shown in Table 5, it was found that, in a case in which a preparation was formed such that the composition ratio (% (v/v)) of polysorbate 80 to polyethylene glycol 300 is within the range of from 55/45 to 45/55, the obtained liquid preparation can be rapidly mixed with the infusion liquid (physiological saline) used for intravenous drip infusion. Furthermore, as is clear from the results shown in Examples 1 to 3, the liquid preparation according to the invention can be completely mixed with the infusion liquid in a short time of less than 1 minute from the start of mixing. That is, it is revealed that the liquid preparation according to the invention is extremely favorable from the viewpoint of practicality in clinical practice.

From the results shown in Tables 3 to 5, it was found that the liquid preparation of docetaxel of Examples 1 to 3 prepared to have the composition ratio (% (v/v)) of polysorbate 80 to polyethylene glycol 300 of from 55/45 to 45/55 can achieve mixability with the infusion liquid without using ethanol, which has not been achieved using the existing drugs such as TAXOTERE (registered trade name) (an injectable drug of a docetaxel hydrate, manufactured by Sanofi-Aventis) and ONETAXOTERE (registered trade name) (an injectable drug of a docetaxel hydrate, manufactured by Sanofi-Aventis).

Furthermore, it was revealed that no precipitation is generated in the liquid preparations of Examples 1 to 3.

Examples 4 and 5 and Reference Example 8

Each of the liquid compositions of Examples 4 and 5 and Reference Example 8 was obtained in the same manner as in Example 1, except that the amounts of the respective components were changed to the amounts shown in Table 6.

Each of vial containers was prepared in which the amount of sodium that leached from the vial container into water when the vial container had been charged with water and heated at 121° C. for 60 minutes was as shown in Table 7. The above-obtained liquid compositions (Examples 4 and 5 and Reference Example 8) were charged into the vial containers, respectively, thereby obtaining respective liquid preparations. The accelerated stability test was conducted at 40° C. and 75% relative humidity for 1 month.

In addition to the liquid compositions of Examples 4 and 5 and Reference Example 8, the liquid composition of Example 1 was charged into the vial container in the same manner as in Example 4, thereby obtaining a liquid preparation according to Example 1. With regard to the liquid preparation according to Example 2, the accelerated stability test was conducted in the same manner as in Example 4.

The stability of the liquid preparation after the accelerated stability test was evaluated based on the production amounts of 7-epi-docetaxel and 10-oxo-docetaxel, which are the main degraded products generated from docetaxel.

With regard to the evaluation, the amounts of the generated degraded products were evaluated by measuring the docetaxel concentration immediately after the preparation of the liquid preparation with high-speed liquid chromatography, and then calculating the ratio of the peak area of docetaxel to the peak area of either of respective degraded products (7-epi-docetaxel and 10-oxo-docetaxel).

As a reference standard of 7-epi-docetaxel, 7-epi-docetaxel manufactured by Toronto Research Chemicals Inc. was used.

As a reference standard of 10-oxo-docetaxel, 10-oxo-docetaxel manufactured by Santa Cruz Biotechnology, Inc. and DOCETAXEL IDENTIFICATION (trade name, manufactured by USP) were used.

The conditions for high-speed liquid chromatography were set as follows.

Column: SHIM-PACK XR-ODSII (manufactured by Shimadzu Corporation)
Detector: UV detector
Detection wavelength: 230 nm
The evaluation result is shown in Table 8.

TABLE 6

|  | Unit | Example 1 | Example 4 | Example 5 | Reference Example 8 |
|---|---|---|---|---|---|
| Polysorbate 80 | mL | 1.0 | 1.0 | 1.0 | 1.0 |
| PEG 300 | mL | 1.0 | 1.0 | 1.0 | 1.0 |
| Anhydrous citric acid | mg | 3.75 | 3.75 | 3.75 | 3.75 |
| Docetaxel trihydrate | mg | 42.7 | 42.7 | 42.7 | 42.7 |
| Vial container |  | Low-temperature treatment | Silicoat treatment | Organic acid treatment | No treatment |

TABLE 7

| Vial container | Amount of Na leaching out [ppm] |
|---|---|
| Low-temperature treatment (Nichiden-Rika Glass Co,. Ltd.) | 0.57 |
| Silicoat treatment (Fuji Glass Co., Ltd) | 0.1 |
| Organic acid treatment (Daiwa Special Glass Co., Ltd.) | 0.19 |
| No treatment (Nichiden-Rika Glass Co,. Ltd.) | 3.31 |

TABLE 8

|  | Amount of Na leaching out [ppm] | 7-epi-docetaxel production amount | | 10-oxo-docetaxel production amount | |
|---|---|---|---|---|---|
|  |  | Immediately after preparation | After accelerated stability test | Immediately after preparation | After accelerated stability test |
| Example 1 | 0.57 | 0.08 | 0.12 | 0.06 | 0.35 |
| Example 4 | 0.1 | 0.10 | 0.09 | 0.06 | 0.31 |
| Example 5 | 0.19 | 0.07 | 0.07 | 0.04 | 0.36 |
| Reference Example 8 | 3.31 | 0.07 | 0.32 | 0.04 | 0.37 |

From the result shown in Table 8, it was found that the production amount of 7-epi-docetaxel, which is a degraded product of docetaxel, can be suppressed by reducing the amount of Na leaching out from the vial container.

Examples 6 and 7 and Reference Example 9

Each of liquid preparations of Examples 6 and 7 and Reference Example 9 was obtained in the same manner as in Example 1, except that the amounts of respective components were changed to the amounts shown in Table 9.

Each of the obtained liquid preparations was charged into a low temperature treated vial container in which the amount of sodium that leaches from the vial container into water was 0.57 ppm when the vial container has been charged with water and heated at 121° C. for 60 minutes, and subjected to the accelerated stability test at 40° C. and 75% relative humidity for 1 month.

In Examples 6 an 7 and Reference Example 9, the peroxide value (meq/L) of the polysorbate 80 was measured in accordance with the method described in EP (European Pharmacopoeia). The measured value of the peroxide value is shown in Table 9.

The stability of the liquid preparation after the accelerated stability test was evaluated based on the production amount of 10-oxo-docetaxel measured with high-speed liquid chromatography.

The measurement condition and the like for high-speed liquid chromatography were the same as those in Example 4. The evaluation result is shown in Table 10.

TABLE 9

|  | Unit | Example 6 | Example 7 | Reference Example 9 |
|---|---|---|---|---|
| Polysorbate 80 | mL | 1.0 | 1.0 | 1.0 |
| PEG 300 | mL | 1.0 | 1.0 | 1.0 |
| Anhydrous citric acid | mg | 3.75 | 3.75 | 3.75 |
| Docetaxel trihydrate | mg | 42.7 | 42.7 | 42.7 |
| Peroxide value of PS80 |  | 2.916 | 0.300 | 21.632 |

TABLE 10

|  | Peroxide value [meq/L] | 10-oxo-docetaxel production amount | |
|---|---|---|---|
|  |  | Immediately after preparation | After accelerated stability test |
| Example 6 | 2.916 | 0.06 | 0.24 |
| Example 7 | 0.3 | 0.04 | 0.09 |
| Reference Example 9 | 21.634 | 0.06 | 0.38 |

From the result shown in Table 10, it was fund that the production of 10-oxo-docetaxel, which is a degraded product of docetaxel, can be significantly suppressed when the peroxide value of polysorbate 80 to be added is 5.0 meq/Kg or less.

Furthermore, it was found that the stability of the liquid composition can be maintained over a long period and the degradation of the taxane-based active ingredient can be suppressed when the liquid preparation containing the specific amount of surfactant component having a peroxide value of 5.0 meq/Kg or less is prepared using the vial container in which the amount of sodium that leaches from the vial container into water was 1 ppm or less when the vial container had been charged with water and heated at 121° C. for 60 minutes.

From these results, it was found that the liquid composition according to the invention can be rapidly mixed into an infusion liquid used for intravenous drip infusion without substantial use of ethanol. Furthermore, it was found that the liquid preparation according to the invention is a highly stable preparation.

Examples 8 and 9

Each of liquid preparations of Examples 8 and 9 was obtained in the same manner as in Example 1, except that the amounts of respective components were changed to the amounts shown in Table 11.

With regard to Examples 8 and 9, the manufacturing suitability was evaluated based on the time required for dissolving and the appearance observation in the same manner as in Example 1. The evaluation result is shown in Table 11. In Table 11, "-" indicates that the component was not added.

In Examples 8 and 9, the average molecular weight of PEG 300 is from 285 to 315, the average molecular weight of PEG 400 is from 380 to 420, and the average molecular weight of PEG 600 is from 570 to 630.

TABLE 11

|  | Unit | Example 1 | Example 8 | Example 9 |
|---|---|---|---|---|
| Polysorbate 80 (PS 80) | mL | 1 | 1 | 1 |
| PEG 300 | mL | 1 | 0.9 | 0.92 |
| PEG 400 | mL | — | 0.1 | — |
| PEG 600 | mL | — | — | 0.08 |
| Propylene glycol | mL | — | — | — |
| Anhydrous citric acid | mg | 3.75 | 3.75 | 3.75 |
| Docetaxel trihydrate | mg | 42.7 | 42.7 | 42.7 |
| Appearance |  | Homogenous solution | Homogenous solution | Homogenous solution |
| Judgement |  | A | A | A |
| Time required for dissolving |  | 2 | 2 | 2 |
| Judgement |  | A | A | A |
| After 1 minute |  | A | A | A |

From the result shown in Table 11, it was found that the glycol is preferably PEG 300 to PEG 600 in order to prepare the homogenous liquid preparation that can be miscible in the infusion liquid in a rapid manner. Furthermore, it was found that the ratio of PEG300 in the glycol is preferably 90% or more from the viewpoint of the production time (time required for dissolving).

Examples 10 to 12 and Reference Examples 10 to 13

Each of liquid preparations of Examples 10 to 12 and Reference Examples 10 to 13 was obtained in the same manner as in Example 1, except that the amounts of respective components were changed to the amounts shown in Tables 12 and 13.

With regard to Examples 10 and 12, the manufacturing suitability was evaluated based on the time required for dissolving and the appearance observation in a manner similar to Example 1. Furthermore, the mixability with the infusion liquid was evaluated in the same manner as in Example 1.

The evaluation results are shown in Table 12.

TABLE 12

|  | Unit | Example 10 | Example 11 | Example 12 |
|---|---|---|---|---|
| Polysorbate 80 (PS 80) | mL | 1 | 1 | 1 |
| PEG 300 | mL | 1 | 1 | 1 |
| Anhydrous citric acid | mg | 2.5 | 5 | 7.5 |
| Docetaxel trihydrate | mg | 42.7 | 42.7 | 42.7 |
| Appearance |  | Homogenous solution | Homogenous solution | Homogenous solution |
| Judgement |  | A | A | A |
| Time required for dissolving |  | 2 | 2 | 2 |
| Judgement |  | A | A | A |
| After 1 minute |  | A | A | A |

With regard to the liquid preparations of Examples 10 to 12 and Reference Examples 10 to 13, the accelerated stability test was conducted at 40° C. and 75% relative humidity for 1 month in the same manner as in Example 4. The stability of the liquid preparation was evaluated by measuring the total amount of the degraded products with high-speed liquid chromatography. The measurement condition and the like for high-speed liquid chromatography were the same as those in Example 4. The evaluation result is shown in Table 13. Here, the total amount of the degraded products means the total production amount of 7-epi-docetaxel and 10-oxo-docetaxel shown in Example 4 and other docetaxel related compounds.

TABLE 13

|  | Unit | Example 1 | Example 10 | Example 11 | Example 12 | Reference Example 10 | Reference Example 11 | Reference Example 12 | Reference Example 13 |
|---|---|---|---|---|---|---|---|---|---|
| Polysorbate 80 (PS 80) | mL | 1 | 1 | 1 | 1 | 1 | 1 | 1 | 1 |
| PEG 300 | mL | 1 | 1 | 1 | 1 | 1 | 1 | 1 | 1 |
| Anhydrous citric acid | mg | 3.75 | 2.5 | 5 | 7.5 | 0 | 1 | 11.3 | 15 |
| Docetaxel trihydrate | mg | 42.7 | 42.7 | 42.7 | 42.7 | 42.7 | 42.7 | 42.7 | 42.7 |
| pH |  | 3.5 | 3.5 | 3.3 | 3 | 6.2 | 4.2 | 2.8 | 2.7 |
| Total amount of degraded products [g] |  | 0.21 | 0.44 | 0.24 | 0.59 | 12.97 | 1.06 | n.t. | n.t. |

* n.t.: not tested

From the results shown in Tables 12 and 13, it was found that the addition amount of citric acid is preferably form 1.25 mg/mL to 3.75 mg/mL in order to obtain the preparation that is less irritating when administered by intravenous drip infusion and has an improved stability of the taxane-based active ingredient.

The disclosure of Japanese Patent Application No. 2012-161001 filed on Jul. 19, 2012, is incorporated herein by reference in its entirety.

All publications, patent applications, and technical standards mentioned in this specification are herein incorporated by reference to the same extent as if each individual publication, patent application, or technical standard was specifically and individually indicated to be incorporated by reference.

The invention claimed is:

1. A liquid composition, comprising:
    at least one taxane-based active ingredient selected from the group consisting of docetaxel and a docetaxel trihydrate;
    polyethyelene glycol 300;
    polysorbate 80; and
    anhydrous citric acid at a concentration of from 1.0 mg/mL to 4.0 mg/mL,
    wherein a volume ratio of the polyethyelene glycol 300 to the polysorbate 80 is in a range of from 47.5/52.5 to 52.5/47.5, and
    a total content of the polyethyelene glycol 300 and the polysorbate 80 with respect to a total volume of the liquid composition is 95% (v/v) or more.

2. The liquid composition according to claim 1, wherein a concentration of the taxane-based active ingredient is from 16 mg/mL to 24 mg/mL.

3. The liquid composition according to claim 1, wherein the polysorbate 80 has a peroxide value of 5 meq/kg or less.

4. The liquid composition according to claim 1, which has a pH within a range of from 3.0 to 4.5 when diluted fivefold with distilled water.

5. The liquid composition according to claim 1, wherein a content of ethanol with respect to a total volume of the liquid composition is less than 1% (v/v).

6. A liquid preparation comprising the liquid composition according to claim 1 contained in a vial container, an amount of sodium that leaches from the vial container into water being 1 ppm or less when the vial container has been charged with water and heated at 121° C. for 60 minutes.

* * * * *